(12) United States Patent
Brown et al.

(10) Patent No.: US 9,107,491 B2
(45) Date of Patent: Aug. 18, 2015

(54) HIGH CLEANING DENTIFRICE COMPOSITIONS

(75) Inventors: James Brown, Edison, NJ (US); Dennis K. Ontumi, Easton, PA (US); Richard Robinson, Belle Meade, NJ (US)

(73) Assignee: Colgate-Palmolive Company, New York, NY (US)

( * ) Notice: Subject to any disclaimer, the term of this patent is extended or adjusted under 35 U.S.C. 154(b) by 663 days.

(21) Appl. No.: 13/386,944

(22) PCT Filed: Jul. 23, 2010

(86) PCT No.: PCT/US2010/043007
§ 371 (c)(1),
(2), (4) Date: Jan. 25, 2012

(87) PCT Pub. No.: WO2011/014415
PCT Pub. Date: Feb. 3, 2011

(65) Prior Publication Data
US 2012/0121316 A1      May 17, 2012

Related U.S. Application Data

(60) Provisional application No. 61/230,321, filed on Jul. 31, 2009.

(51) Int. Cl.
*A61K 8/00* (2006.01)
*A61Q 11/00* (2006.01)
(Continued)

(52) U.S. Cl.
CPC ........... *A46B 11/0003* (2013.01); *A46B 11/001* (2013.01); *A46B 11/0041* (2013.01); *A46B 11/0065* (2013.01); *A46B 15/0091* (2013.01);
(Continued)

(58) Field of Classification Search
CPC .................. A46B 11/0003; A61K 6/0008
See application file for complete search history.

(56) References Cited

U.S. PATENT DOCUMENTS 2,778,045 A    1/1957    Ely et al.
3,165,776 A    1/1965    Tussth
(Continued)

FOREIGN PATENT DOCUMENTS

CN    1606532    4/2005
GB    1567454    5/1980
(Continued)

OTHER PUBLICATIONS

Zimmer et al., 2000, "Fluoride release from a toothbrush," J. Clinical Dentistry 11(4):114-117.
(Continued)

*Primary Examiner* — David Walczak
*Assistant Examiner* — Joshua Wiljanen

(57) ABSTRACT

A dentifrice composition containing minor amounts of relatively small particle size high cleaning abrasives, without oral care actives. The dentifrice may be encapsulated and optionally, positioned on the head of a toothbrush. Use of the dentifrice provides a small amount of high cleaning abrasive to the teeth, and has stain removal efficacy. In one aspect, a dentifrice composition comprising an orally acceptable carrier and 1 to 10 wt % abrasive, such that the total amount of abrasive delivered per application is 2 mg to 8 mg, the abrasive having a weight mean particle size in the range of 3 to 7 μm, with at least 90% of the particles by weight having a size below 16 μm, and wherein the composition does not contain an oral care active.

24 Claims, 6 Drawing Sheets

(51) Int. Cl.
  *A46B 11/00* (2006.01)
  *A61K 6/00* (2006.01)
  *A46B 15/00* (2006.01)
  *A61K 8/25* (2006.01)
  *A61K 8/37* (2006.01)

(52) U.S. Cl.
  CPC ........... *A46B 15/0093* (2013.01); *A61K 6/0008* (2013.01); *A61K 8/25* (2013.01); *A61K 8/375* (2013.01); *A61Q 11/00* (2013.01); *A46B 2200/1066* (2013.01); *A61K 2800/28* (2013.01); *A61K 2800/412* (2013.01)

(56) References Cited

U.S. PATENT DOCUMENTS

| | | | |
|---|---|---|---|
| 3,231,925 A | 2/1966 | Conder | |
| 3,302,230 A | 2/1967 | Poppelman | |
| 3,378,870 A | 4/1968 | Matsunaga | |
| 3,691,585 A | 9/1972 | Flom | |
| 3,952,867 A | 4/1976 | McCord | |
| 4,030,845 A | 6/1977 | Deckert | |
| 4,153,680 A | 5/1979 | Seybert | |
| 4,187,288 A * | 2/1980 | Cordon et al. | 424/49 |
| 4,340,583 A | 7/1982 | Wason | |
| 4,420,312 A | 12/1983 | Wason | |
| 4,421,527 A | 12/1983 | Wason | |
| 4,422,985 A | 12/1983 | Morishita et al. | |
| 4,426,337 A | 1/1984 | Suzuki et al. | |
| 4,632,826 A | 12/1986 | Ploger et al. | |
| 4,929,180 A | 5/1990 | Moreschini | |
| 4,943,429 A | 7/1990 | Winston et al. | |
| 5,176,899 A | 1/1993 | Montgomery | |
| 5,184,719 A | 2/1993 | Gordon | |
| 5,213,428 A | 5/1993 | Salman | |
| 5,270,033 A | 12/1993 | Montgomery | |
| 5,300,290 A | 4/1994 | Spencer | |
| 5,320,842 A | 6/1994 | Spencer | |
| 5,348,473 A | 9/1994 | Kivlighan, Jr. | |
| 5,390,984 A | 2/1995 | Boucherie et al. | |
| 5,393,796 A | 2/1995 | Halberstadt et al. | |
| 5,478,570 A | 12/1995 | Sunphara et al. | |
| 5,533,791 A | 7/1996 | Boucherie | |
| 5,603,920 A | 2/1997 | Rice | |
| 5,604,951 A | 2/1997 | Shipp | |
| 5,605,756 A | 2/1997 | Sanduja et al. | |
| 5,609,890 A | 3/1997 | Boucherie | |
| 5,651,958 A | 7/1997 | Rice | |
| 5,658,553 A | 8/1997 | Rice | |
| 5,783,249 A | 7/1998 | Sanduja et al. | |
| 5,836,769 A | 11/1998 | Spencer | |
| 5,888,578 A | 3/1999 | Sanduja et al. | |
| 5,939,051 A | 8/1999 | Santalucia et al. | |
| 6,004,059 A | 12/1999 | Zaccaria | |
| 6,471,945 B2 | 10/2002 | Luo et al. | |
| 6,479,071 B2 | 11/2002 | Holme et al. | |
| 6,524,023 B2 | 2/2003 | Andersen | |
| 6,669,929 B1 | 12/2003 | Boyd et al. | |
| 6,682,722 B2 | 1/2004 | Majeti et al. | |
| 6,696,044 B2 | 2/2004 | Luo et al. | |
| 6,896,876 B1 | 5/2005 | Libanati et al. | |
| 7,182,542 B2 | 2/2007 | Hohlbein | |
| 7,267,814 B2 | 9/2007 | McGill et al. | |
| 7,306,788 B2 | 12/2007 | McGill et al. | |
| 7,331,731 B2 | 2/2008 | Hohlbein et al. | |
| 7,445,796 B2 | 11/2008 | Holme et al. | |
| 7,575,387 B2 | 8/2009 | Atkin | |
| 2004/0175334 A1 | 9/2004 | MacKinnon | |
| 2004/0237226 A1 | 12/2004 | Hohlbein et al. | |
| 2005/0069372 A1 | 3/2005 | Hohlbein et al. | |
| 2005/0129628 A1 | 6/2005 | Stanier et al. | |
| 2006/0008422 A1 | 1/2006 | Araya et al. | |
| 2006/0008423 A1 | 1/2006 | Araya et al. | |
| 2007/0140985 A1 | 6/2007 | Boyd et al. | |
| 2008/0120798 A1 * | 5/2008 | Sorrentino et al. | 15/106 |
| 2009/0010973 A1 | 1/2009 | Stanier | |
| 2009/0068122 A1 * | 3/2009 | Pilch et al. | 424/49 |

FOREIGN PATENT DOCUMENTS

| | | |
|---|---|---|
| GB | 2038303 | 7/1980 |
| JP | H08-169811 | 7/1996 |
| JP | H09-5248 | 9/1997 |
| JP | 2006-509768 | 3/2006 |
| JP | 2008-509225 | 3/2008 |
| RU | 2275219 | 4/2006 |
| RU | 2355183 | 5/2009 |
| WO | WO 03/055802 | 7/2003 |
| WO | WO 2004/028500 | 4/2004 |
| WO | WO 2007/068916 | 6/2007 |

OTHER PUBLICATIONS

Grabenstetter et al., "The measurement of the abrasion of human teeth by dentifrice abrasives: a test utilizing radioactive teeth," Journal of Dental Research, 37(6):1060-8, Nov./Dec. 1958.

Hefferren, "A Laboratory Method for Assessment of Dentifrice Abrasivity," Journal of Dental Research, 55:563-573, Jul. 1976.

Stookey et al., "In vitro removal of stain with dentifrices," Journal of Dental Research 61(11):1236-9, Nov. 1982.

International Search Report and Written Opinion for International Application No. PCT/US2010/043007 mailed Nov. 30, 2010.

* cited by examiner

180# HIGH CLEANING DENTIFRICE COMPOSITIONS

CROSS REFERENCE TO RELATED APPLICATIONS

This application is a national stage entry under 35 U.S.C. §371 of International Patent Application No. PCT/US2010/043007, filed 23 Jul. 2010, which claims priority to U.S. Provisional Patent Application Ser. No. 61/230,321, filed on 31 Jul. 2009, the entireties of which are incorporated herein by reference.

BACKGROUND

The embodiments relate to dentifrice compositions containing minor amounts of relatively small particle size high cleaning abrasives, without antibacterial agents, fluorides, and other oral care actives. In particular, dentifrice compositions having good stain removal characteristics. The dentifrice compositions can be in the form of encapsulated compositions, solid confectionary compositions, gums, and the like, which optionally may be positioned within the bristles of a tooth brushing device.

Conventional abrasives include silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate, sodium tripolyphosphate (STPP), tetrasodium pyrophosphate (TSPP), and insoluble sodium polymetaphosphate. One or more abrasives typically are present in a dentifrice in an abrasive effective total amount, typically 5% to 70%, for example 10% to 50% or 15% to 30% by weight of the composition. The average particle size of an abrasive is generally 0.1 to 30 µm, for example 1 to 20 µm or 5 to 15 µm.

Synthetically produced silicas play an important role as an ingredient in many of today's toothpaste formulations. Such silicas are relatively safe, nontoxic, ingredients which are compatible with other toothpaste ingredients, including glycerin, sorbitol (or xylitol), thickening agents, detergents, coloring and fragrance materials and optionally fluoride and other actives, whereby the silica acts as an abrasive to clean teeth, remove plaque and food debris.

As an abrasive, silicas debride and physically scrub the external surface of the teeth. This scrubbing action removes the organic film (i.e. the pellicle), formed of salivary proteins which covers the teeth and which is known to become stained and discolored by foods, such as coffee, tea and berries, as well as, by tobacco smoke, cationic antibacterials, and chromogenic bacteria. Such physical removal of the stained pellicle is a simple and effective means of removing the undesirable surface staining and discoloration which occurs daily. Further, such physical removal of the pellicle also removes plaque bacteria on the pellicle surface.

Synthetic silicas include both silica gels and precipitated silicas which are prepared by the neutralization of aqueous silicate solutions with a strong mineral acid. In the preparation of silica gel, a silica hydrogel is fanned which is then typically washed to low salt content. The washed hydrogel may be milled to the desired size, or otherwise dried, ultimately to the point where its structure no longer changes as a result of shrinkage. When preparing such synthetic silicas, the objective is to obtain abrasives which provide maximal cleaning (i.e. removal of stained pellicle) with minimal damage to the tooth enamel and other oral tissue. Dental researchers are continually concerned with identifying synthetic silicas meeting these objectives.

U.S. Pat. No. 4,153,680 and GB Patent Application 2,038,303A both disclose the general use of silica hydrogels or hydrated silica gels as dentifrice polishing agents. U.S. Pat. No. 4,632,826 discloses the use of hydrated silica gels in combination with a weakly calcined alumina polish, to form a combination abrasive system. U.S. Pat. Nos. 4,943,429, 5,176,899 and 5,270,033 provide lists of alternative polishing agents, such lists including hydrated silica gels.

U.S. Pat. No. 5,939,051 discloses dentifrice compositions prepared with silica gels having low abrasion and high cleaning products. However, the silica gels have a low particle size distribution of from 2 to 4 microns in order to achieve the low abrasive properties. Manufacturing such small particle size silica gel is energy intensive and relatively costly.

U.S. Pat. Nos. 5,658,553 and 5,651,958 disclose dentifrice compositions containing a combination of precipitated silica and silica gels having high cleaning and low abrasion as indicated by their low radioactive dentin abrasion (RDA) values. Due to the low abrasive nature of the silicas described in U.S. Pat. Nos. 5,651,958 and 5,658,553 the composition inherently has limited cleaning ability.

RDA value is a dental art recognized method of determining the abrasiveness of dentifrice formulations and is determined according to the method recommended by the American Dental Association as set forth by Hefferren, Journal of Dental Research, Volume 55, Issue 4, July-August 1976, pp. 563-573, and described in the Wason U.S. Pat. Nos. 4,340,583, 4,420,312 and 4,421,527.

It is known in the dental art that increasing the RDA value of a dentifrice composition above 110 does not result in a corresponding increase in the cleaning performance of the dentifrice, as measured by Pellicle Cleaning Ratio (PCR), an in vitro method used to measure the efficacy of removing tea and coffee tooth stains relative to a standard. The PCR values referred to herein are obtained by a modification of the method described in "In Vitro Removal of Stain with Dentifrice", G. K. Stookey, et al *J. Dental Research,* 61, 123-9, 1982. The modification of the PCR method used herein is described in U.S. Pat. Nos. 5,658,553 and 5,651,958. In this modification, a clear pellicle material is applied to a bovine tooth first, which is then stained with a combination of the pellicle material and tea, coffee and $FeCl_3$ whereas in the original method described by Stookey et al, both pellicle and stain are applied simultaneously.

Silica particles referred to as "high cleaning" silica are known and described in, for example, U.S. Pat. Nos. 7,306,788, 7,267,814, 6,896,876, 6,669,929. Many of these are commercially available from J. M. Huber (Havre de Grace, Md. USA), sold under the trade name Zeodent™. Other silicas are designed to replace a portion of conventional silicas to enhance or boost their cleaning efficacy, as described in, for example, U.S. Patent Application Publication Nos. 2009/0010973, 2006/0008423, 2006/0008422, 2005/0129628.

Dentifrice compositions in the form of solid, semi-solid, or encapsulated compositions positioned within the bristles of a tooth brushing device are known. Colgate® WISP™ is one such device. The Wisp device is a small tooth brushing device (about 8.9 cm (3.5 inches)) in length) that includes a gelatin encapsulated liquid composition positioned within the bristles. The liquid capsule releases a burst of freshness when used, without the need for water or rinsing. The Wisp is designed to be used once, and then discarded.

There remains a need to provide a dentifrice composition that is not necessarily intended to be used as a toothpaste or gel, that does not necessarily contain oral care actives, and that is effective in removing stains and cleaning teeth.

BRIEF SUMMARY

Various embodiments described herein satisfy the aforementioned needs, by providing dentifrice compositions having improved stain removal and teeth cleaning efficacy.

According to one aspect, dentifrice compositions comprising an orally acceptable carrier and minor amounts of relatively small particle size abrasives, preferably without antibacterial agents, fluorides, and other oral care actives. The compositions may be present as a gel, solid, encapsulated in a gelatin capsule, or present as aqueous or anhydrous compositions.

According to another aspect, dentifrice compositions are provided as solid or encapsulated compositions, positioned within the bristles of a tooth brushing device. In a preferred aspect, the compositions are designed for a one-time use and then disposal of the tooth brushing device.

According to yet another aspect, there is provided a method of making the dentifrice compositions comprising mixing an orally acceptable carrier, flavors, sweeteners, and optionally an alcohol processing aid to produce a liquid composition, and adding to the liquid composition a minor amount of small particle size abrasive. In another embodiment, the dentifrice composition is encapsulated with a gelatin outer capsule, wherein the alcohol processing aid is removed from the composition during encapsulation. In another embodiment, the encapsulated composition then is positioned within the bristles of a tooth brushing device.

In one embodiment, a dentifrice composition comprising an orally acceptable carrier and 1 to 10 wt % abrasive, such that the total amount of abrasive delivered per application is 2 mg to 8 mg, the abrasive having a weight mean particle size in the range of 3 to 7 µm, with at least 90% of the particles by weight having a size below 16 µm, and wherein the composition does not contain an oral care active.

In another embodiment, a method of making a dentifrice composition comprising mixing an orally acceptable carrier, flavors, sweeteners, and optionally, a processing aid to form a liquid mixture, and adding to the liquid mixture 1 to 10 wt % abrasive having a mean particle size in the range of 3 to 7 µm, with at least 90% of the particles by weight having a size below 16 µm, without mixing or adding an oral care active.

In another embodiment, a toothbrush comprising: a handle; a head mounted to the handle, the head comprising an outer surface and a plurality of tooth cleaning elements extending outwardly from the outer surface; and a dentifrice composition positioned on the head, the dentifrice composition comprising an orally acceptable carrier and 1 to 10 wt % abrasive, such that the total amount of abrasive delivered per application is 2 mg to 8 mg, the abrasive having a weight mean particle size in the range of 3 to 7 µm, with at least 90% of the particles by weight having a size below 16 µm.

DETAILED DESCRIPTION

Figure 1:
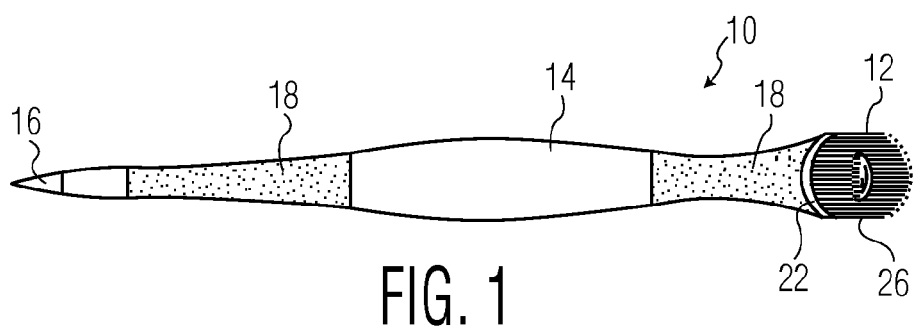
FIG. 1 is a front view of an oral care toothbrush comprising a capsule comprising a dentifrice composition in accordance with an embodiment.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, terms "treatment" or "treating" are intended to include prophylaxis. The terms include amelioration, prevention and relief from the symptoms and/or effects associated with oral malodor. The terms "preventing" or "prevention" refer to administering the composition beforehand to forestall or obtund oral malodor. Persons of ordinary skill in the art of compositions for the treatment of oral malodor (to which the present method claims are directed) recognize that the term "prevent" is not an absolute term. Rather, the term is understood to refer to the prophylactic administration of a composition to diminish the likelihood or seriousness of a condition, and this is the sense intended.

An "orally acceptable amount" of a compound is an amount that is not harmful to a mammal when a composition containing such amount is retained in the mouth, without swallowing, for a period sufficient to permit application to an oral surface as provided herein. In general, such amount of the compound is not harmful even if the composition is unintentionally swallowed. An "orally acceptable carrier" denotes any vehicle or carrier that is not harmful to a mammal when such carrier is used in a composition that is retained in the mouth, without swallowing.

Formulated dentifrices such as tooth pastes and gels contain a number of functional and active ingredients, each of which contribute to one or a number of desirable properties. Properly formulated dentifrices are suitable for regular use to promote oral health. Functional additives include foaming agents that disperse other ingredients and provide for delivery of the active and functional materials to the oral surfaces, and tartar control agents to prevent the formation of calculus on tooth surfaces, as well as aesthetic functional ingredients such as flavors and pigments. Active ingredients include anticaries agents that provide a source of fluoride ion upon use. Various compositions also contain compounds or components with antibacterial properties, for example to reduce the formation of plaque on the surfaces. Further active ingredients include those with anti-inflammatory properties for prophylaxis and treatment of conditions such as gingivitis. Other than flavors and pigments, preferred dentifrice compositions do not include any of the aforementioned oral care active components.

Throughout this description, the expression "oral care active" denotes a component that provides an active effect during an oral care treatment. Oral care actives include, but are not limited to foaming agents, antibacterial agents, whitening agents, anti-calculus agents, antimicrobial agents, tartar control agents, anti-inflammatory agents, and the like.

In a first aspect, the dentifrice composition comprises, consists essentially of, or consists of 1 to 10 wt %, preferably 2.5 to 7 wt %, and most preferably 5 wt % high cleaning abrasive, such that the total amount of abrasive delivered per application is 2 mg to 8 mg, preferably 3 mg to 6 mg, and most preferably about 4 mg of abrasive. The high cleaning abrasive is present in an orally acceptable carrier. The present inventors discovered that use of such a small amount of small particle size abrasive achieved an unexpectedly improved stain removal effect, because such minor amounts of abrasive would not normally have been expected to provide any stain removal effect (or at the very least, very little stain removal). The dentifrice compositions preferably do not contain oral care actives, such as antibacterial agents, malodor prevention agents, anti caries agents, whitening agents such as peroxides, tartar control agents, and the like.

It is preferred that the abrasive be selected from high cleaning silica, tetrasodium pyrophosphate (TSPP), sodium tripolyphosphate (STPP), and mixtures thereof. The abrasives typically have a weight mean particle size in the range 2 to 18 µm with at least 90% by weight of particles having a size below 20 µm, a Radioactive Dentine Abrasion (RDA) determined on an aqueous slurry of the silica powder of 90 to 230, a Pellicle Cleaning Ratio (PCR), when incorporated in a dental composition at 10% by weight, greater than 80, the ratio of PCR to RDA being in the range 0.4:1 to less than 1:1 and having a Plastics Abrasion Value (PAV) in the range of 1 to 20.

The preferred abrasives are silicas having a particularly effective ability to clean, which is demonstrated by relatively high PCR values exhibited at conventional RDA values in dentifrices containing a relatively small amount of the silica. Although the PCR to RDA ratio is less than 1, the RDA value preferably is higher than conventional silicas with a higher PCR to RDA ratio and, when compared to these products, a higher PCR is achievable with the same quantity of silica. Plastics Abrasion Values are a measure of the amount of scratching produced on a surface by the silica and are therefore indicative of possible damage to teeth. The silicas useful possess a moderate PAV but high PCR, which indicates good cleaning without excessive damage.

The amorphous silicas useful preferably have an oil absorption, using linseed oil, in the range 70 to 150 cm$^3$/100 g and, more preferably, the oil absorption is in the range 75 to 130 cm$^3$/100 g. Also, the amorphous silica preferably has a BET surface area in the range 10 to 450 m$^2$ g$^{-1}$, and, more preferably, the BET surface area is in the range 50 to 300 m$^2$ g$^{-1}$.

The weight mean particle size of the silica can be determined using a Malvern Mastersizer™ and a preferred material may have a weight mean particle size in the range 5 to 10 µm. The particle size distribution and, hence, the proportion of particles having a size below any particular value can be determined by the same technique. For the amorphous silica, at least 90% of the particles by weight preferably have a size below 17 µm.

In a particular embodiment, the weight mean particle size of the abrasives useful in the embodiments is in the range of 3 to 7 µm, with at least 90% of the particles by weight having a size below 16 preferably below 12 µm.

The Radioactive Dentine Abrasion (RDA) of the silicas has a value in the range 100 to 220. More commonly, the RDA has a value in the range 120 to 200 and, frequently, the RDA is above 140. Generally, silicas having a PAV above 15 will have an RDA above 120 and those having a PAV above 17 have an RDA above 140.

The PCR (measured in a dental composition at 10% by weight) of the amorphous silica is greater than 85, preferably greater than 90 and more preferably greater than 95. The PCR:RDA ratio is preferably in the range 0.5:1 to 0.9:1.

The amorphous silica preferably has a pH value, measured on a 5% by weight suspension, in the range 5 to 8, more preferably in the range 6 to 7.5. The amount of water present on the amorphous silica suitable for use in a dental composition, as measured by the ignition loss at 1000° C., is usually up to 25% by weight and preferably up to 15% by weight. Usually the ignition loss at 1000° C. is more than 4% by weight.

In addition to the abrasive material, the dentifrice compositions may also contain one or more orally acceptable flavorants, colorants, sweeteners, processing aids (alcohols such as ethanol), and optionally water. Preferred orally acceptable carriers include, for example, alcohols, medium chain triglycerides, and the like. Most preferably, the carrier is a medium chain triglyceride, and is present in an amount of 50% to 90% by weight, more preferably from 60% to 80%, and most preferably about 75% by weight of the composition. Medium chain triglycerides (MCT) are typically about 6 to about 12 carbons in length. Medium chain triglycerides can be vegetable oils.

Colorants such as pigments and dyes may be used in the composition. Pigments include nontoxic, water insoluble inorganic pigments such as titanium dioxide and chromium oxide greens, ultramarine blues and pinks and ferric oxides. The pigments have a particle size in the range of 5-1000 microns, preferably 250-500 microns, and are present at a concentration of 0.5 to 3% by weight.

Dyes used are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of ethyl-[4-[[4-

[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium), FD&C Blue No. 1 (disodium salt of dibenzyldiethyldiaminotriphenyl-carbinol trisulfonic acid of indigotin) and mixtures thereof in various proportions. The concentration of the dye for the most effective result is present in the dentifrice composition in an amount 0.0005 to 1% of the total weight.

Any suitable flavoring or sweetening material may also be incorporated in the second dentifrice component. Examples of suitable flavoring constituents include flavoring oils, as for example, oils of spearmint, peppermint, wintergreen, sassafras, clove, sage, eucalyptus, marjoram, cinnamon lemon, and orange, and methyl salicylate. Suitable sweetening agents include sucrose, sucralose, lactose, maltose, sorbitol, xylitol, sodium cyclamate, perillatine, and sodium saccharin. Suitably, flavoring materials are included in the dentifrice composition in an amount of 5% to 25% by weight, more preferably 10% to 20% by weight, and most preferably about 15% by weight. The sweetening agents may comprise 0.1 to 5% by weight, more preferably 0.25 to 2% by weight, and most preferably about 0.5% by weight of the dentifrice components.

In various embodiments, the dentifrice compositions contain relatively low amounts of water. In many aspects, the dentifrice compositions contain less water than typical of current commercial formulations. In one embodiment, the compositions contain less than 10% by weight water, for example less than 8% by weight and less than 6% by weight water. The total amount of water in the dentifrice compositions includes contributions from water intentionally added as a component and water present as a byproduct or solvent for various other components. In various embodiments, the dentifrice compositions are formulated without adding water as a separate component. The resulting water content of the dentifrice composition is then derived from the residual water present as solvent or byproduct in the various components. As discussed above, a formulated dentifrice generally contains 10% or less by water, preferably less than 8% and more preferably less than 6%. Most preferably, no water is added to the composition, but the individual components that make up the composition may contain water.

The oral compositions optionally contain one or more other non-active ingredients. Non-limiting examples include diluents, bicarbonate salts, pH modifying agents, foam modulators, thickening agents, viscosity modifiers, pigmenting agents, sweeteners, flavorants and colorants. Tooth pastes, tooth gels, and other dentifrice compositions are formulated with these and optionally other additives according to known principles.

In a preferred aspect, the dentifrice composition is encapsulated into a gelatin capsule. Encapsulating liquid or aqueous compositions in a gelatin capsule can be accomplished using techniques known in the art and described in, for example, U.S. Pat. Nos. 4,422,985, 4,426,337, 5,478,570. The process typically entails forming a jet of the dentifrice composition and a jet of the coating material (e.g., gelatin) coaxial with the jet of dentifrice composition, heating the coaxial jets (optionally with a third coaxial heating element or hot air) and introducing the components into a cooling liquid to form capsules formed of the dentifrice composition, coated with the gelatin. Any alcohol present in the dentifrice preferably is evaporated during the heating of the respective components. Preferably, the gelatin comprises from 6 to 15% of the total weight of the encapsulate, more preferably 8 to 12%, and most preferably about 9%. Similarly, the dentifrice composition comprises 85 to 94% of the total weight of the encapsulate, more preferably 88 to 92, and most preferably about 91%.

In one aspect the dentifrice composition is in the form of a chewing gum. Formulating dentifrice compositions into chewing gums can be accomplished by using a gum base, surfactants, chelating agents, and the like. Any of the methods disclosed in U.S. Pat. Nos. 5,603,920, 6,471,945, 6,479,071, 6,696,044, 7,445,769 can be used to prepare the gum compositions. Other aspects include dentifrice compositions in the form of solid or semi-solid confectionary products. A person having ordinary skill in the art is capable of formulating a solid confectionary product, using the guidelines provided herein.

The composition has been described above with respect to several preferred embodiments. Further non-limiting description is provided in the Examples that follow.

EXAMPLES

Example 1

The compositions of the invention were compared to control compositions using an in-vitra stain removal study in which stain removal was determined by a procedure using extracted bovine teeth. The procedure was similar to that described by Stookey, et al., In vitro removal of stain with dentifrices, *J. Dent Res* 61 (11): 1236-1239, November 1982.
Sample Preparation Squares of dental enamel, 4 mm on a side, were prepared using a diamond cutting disk from bovine permanent incisors. Using a mold, each enamel square was embedded in clear, fast-curing orthodontic resin (Ortho-Jet, Lang Dental Mfg. Co., Inc., Wheeling, Ill.) to provide a 1.5-cm square block with the labial surface exposed. The top surface of the polyester blocks was ground flush with the leveled labial surface of the enamel squares by means of a dental model trimmer. The surface was then smoothed by hand-sanding on 400 grit emery paper using water as the lubricant until all grinding marks were removed. Finally, the top surface of each tooth specimen was hand-polished to a mirror finish using a water slurry of calcined kaolin (median particle size of 1.2 microns) on a cotton cloth. The finished specimens were examined under a dissecting microscope, and were discarded if any imperfections in the enamel surface were observed.

In preparation for the formation of artificial stained pellicle on the enamel, the specimens were etched for 60 seconds in 0.2M HCl followed by a 30-second immersion in a saturated solution of sodium carbonate. A final etch was performed with 1% phytic acid for 60 seconds, then the specimens were rinsed with deionized water and attached to the staining apparatus.
Staining Apparatus The pellicle staining apparatus was constructed to provide alternate immersion into the staining broth and air drying of the specimens. The apparatus consisted of an aluminum platform base which supported a Teflon rod (1.9 cm (¾-inch) in diameter) connected to an electric motor, which by means of a speed reduction box, rotated the rod at a constant rate of 1.5 rpm. Threaded screw holes were spaced at regular intervals along the length of the rod. The tooth specimens were attached to the rod by first gluing the head of a plastic screw to the back of the specimen, then screwing the tooth onto the rod. Beneath the rod was a removable, 300 ml. capacity trough that held the pellicle staining broth.

Staining Broth

The pellicle staining broth was prepared by adding 1.02 gm of instant coffee, 1.02 gm of instant tea, and 0.75 gm of gastric mucin (National Biochemicals Corp., Cleveland, Ohio) to 250 ml of sterilized trypticase soy broth. Approximately 50 ml of a 24-hour *Micrococcus leteus* culture were also added to the stain broth. The apparatus, with the enamel specimens attached and the staining broth in the trough, was then placed in an incubator at 37° C. with the specimens rotating continuously through the staining broth and air. The staining broth was replaced once every 24 hours for 7-10 consecutive days until the desired level of staining was attained. With each broth change the specimens and trough were rinsed and brushed with deionized water to remove any loose deposits. Upon the appearance of yellowish deposits (after 3-5 days), the staining broth was modified by the addition of 0.03 gm $FeCl_3 6H_2O$, and this was continued with daily broth changes until the stained pellicle film on the specimens was sufficiently dark. Then, the specimens were removed from the staining broth, brushed thoroughly with deionized water, and refrigerated in a humidor until used.

Stain Measurement

The intensity of the extrinsic stained pellicle on the teeth was measured by taking diffuse reflectance absorbance readings with a Minolta spectrophotometer. Absorbence measurements over the entire visible color spectrum were obtained using the CIELAB color scale (CIE publication No. 15.2. *CIE Colorimetry*, $2^{nd}$ Ed. Paris: Central Bureau of the CIE, 1986). The stained enamel specimens were allowed to air-dry at room temperature for 30 minutes before absorbance measurements were made.

Treatment

In preparation for treatment, the specimens were stratified into two equal groups of 16 specimens, with each group having equivalent average baseline L*a*b* stain scores. The testing was performed by means of a V-8 mechanical cross-brushing machine designed for the evaluation of standard manual toothbrushes and toothpastes (Grabenstetter, R. J., et al., The measurement of the abrasion of human teeth by dentifrice abrasives: A test utilizing radioactive teeth. *J Dent Res* 37:1060-1068, 1958). A jig was devised to hold the smaller minibrushes used in the Colgate® WISP™ products.

After taking the pre-test spectrophotometer reflectance absorbance readings, the tooth specimens were soaked in artificial saliva for 20 minutes prior to each brushing cycle. Then, the specimens were positioned on the V-8 mechanical cross-brushing machine, and the test products were used to brush the tooth specimens for 2 minutes (i.e., ~300 double strokes). To minimize mechanical variables, tooth specimens for each group were brushed during each run, and the test products were randomly assigned to each brush station until all products had been tested twice at all eight stations. This process was repeated on the tooth specimens with a new brush for each treatment cycle until a total of 14 cycles were completed (i.e., a cumulative treatment time of 28 minutes).

After the final treatment cycle the specimens were pumiced using a dental handpiece in order to remove all residual stain from the teeth, and reflectance absorbance readings were taken again. This technique provided an intrinsic value for each specimen that was used to calculate the maximum amount of stained pellicle that potentially could be removed by the test products.

The mini tooth brushes were prepared by positioning about 65 mg of various test compositions (described below) into the bristles of the mini brushes. The amount of abrasive, if used, was 3 to 6 mg. The ΔE values were measured for each time point. The increase in tooth whiteness (ΔE) was calculated using the following formula:

$$\Delta E = [(\Delta L)^2 + (\Delta a)^2 + (\Delta b)^2]^{1/2}$$

In the above formula, the higher the value of ΔE, the higher is the level of achieved tooth whiteness. Multiple readings were taken on multiple teeth, and the average of ΔE values was calculated.

The difference-between the pre-test and post-test readings for each color factor (L*, a*, and b*) represented the ability of the test dentifrice to remove extrinsic stain from the teeth. The data were calculated and defined as follows:

Stain Removed=Baseline stain reading minus the reading after treatment.

Total Stain Available=Pre-test stain reading minus the reading following treatment and pumicing.

% Total Stain Removed="Stain Removed" divided by "Total Stain Available."

In order to calculate the percent of stain removed by the products, it was necessary to remove all the remaining extrinsic stain by pumicing the teeth totally clean. The ΔL* and ΔE scores obtained after complete stain removal represent the total amount of extrinsic stain available on the teeth for removal by the test products. By comparing these ΔL* and ΔE values with the final ΔL* and ΔE scores obtained after brush treatment, percentages of stain removal were calculated for the two parameters.

The control used to compare to the inventive composition was formulated as shown in Table 1 below:

TABLE 1

| Material | Weight % |
| --- | --- |
| Medium Chain Triglyceride | 78.5 |
| Flavor | 15 |
| WS-3 | 1.5 |
| Sucralose | 0.5 |
| Ethanol* | 4.5 |

The compositions according to the invention were prepared by adding to the control, the high cleaning abrasives. For example, the 5% high cleaning silica (5% HCS) composition was formulated as shown in Table 2 below.

TABLE 2

| Material | Weight % |
| --- | --- |
| Medium Chain Triglyceride | 75 |
| Flavor | 15 |
| AC-43 Silica—high cleaning silica commercially available from PQ Corporation, Malverne, PA, USA | 5 |
| Sucralose | 0.5 |
| Ethanol* | 4.5 |

This composition was labeled HCS 5%. Other compositions were prepared in which the abrasive was changed, and a comparative composition also was used in which no abrasive was used—referred to as the WISP™ formulation. The following abrasives were substituted for the AC-43 Silica (or a different amount was used, in which case the amount of medium chain triglyceride was modified):

2.5% High Cleaning Silica in the core composition
10% High Cleaning Silica in the core composition 2.5% High Cleaning Silica+2.5% Tetrasodium Pyrophosphate (TSPP) in the core composition 5.0% Sodium Tripolyphosphate (STPP)+10.0% Tetrasodium Pyrophosphate (TSPP)

2.5% Tetrasodium Pyrophosphate (TSPP) in the core composition 5.0% Tetrasodium Pyrophosphate (TSPP) in the core composition 10% Sodium Tripolyphosphate (STPP) in the core composition These compositions were tested as described above, and the ΔE values for each composition are provided in Table 3 below:

TABLE 3

| Product | Average<br>$(\Delta E = (\Delta L^2 + \Delta b^2 + \Delta a^2)^{1/2})$ |
| --- | --- |
| Control | 8.8 |
| With Tap water | 3.8 |
| Rubber bristle brush | 8 |
| 2.5% HCS | 9.7 |
| 5.0% HCS | 12.1 |
| 10% HCS | 10.3 |
| 5% STPP | 6.1 |
| 10% STPP | 10.1 |
| 2.5% TSPP | 9.2 |
| 5% TSPP | 9.5 |
| 10% TSPP | 9.7 |
| 2.5% TSPP & 2.5% HCS | 13.8 |

As seen in the above table, the compositions containing only a very small amount of high cleaning abrasive (3-6 mg per application) resulted in remarkably superior stain removal, when compared to the control. A person having ordinary skill in the art would not have expected such minor amounts of abrasives to provide any appreciable effect, much less an effect showing an improvement of from 20% to almost 60% greater stain removal, when compared to the control with no abrasive.

After only a single 2-minute brushing, the inventive samples removed approximately 12% of the extrinsic stain, as compared to 3% for the Control. After 28 minutes of cumulative treatment, the inventive samples removed approximately 40% of the extrinsic stain, as compared to less than 20% for the control. The differences between the inventive samples and the control were statistically significant.

Toothbrush Including Dentifrice

In one preferred aspect, the aforementioned dentifrice, whether being an encapsulated dentifrice, solid dentifrice or gum dentifrice is positioned on an oral care toothbrush. For example, the dentifrice can be positioned on the head of the oral care toothbrush. This can be accomplished by positioning the encapsulated dentifrice, solid dentifrice or gum dentifrice within or between the cleaning elements of the oral care toothbrush. In other embodiments, this can be accomplished by coating, impregnating or otherwise incorporating or fixing the dentifrice to the cleaning elements of the oral care toothbrush. These concepts will be described below in greater detail below with reference to the drawings. When applied to such a tooth brushing device, the amount of dentifrice typically ranges 45 mg to 80 mg, preferably 50 mg to 75 mg, and most preferably about 64 mg of dentifrice.

Referring now to FIGS. 1-4 concurrently, an embodiment of an oral care toothbrush on which the inventive dentifrice can be positioned is illustrated. When the inventive dentifrice is in the form of an encapsulated dentifrice, a solid dentifrice or a gum dentifrice, the inventive dentifrice is preferably positioned either within or between the cleaning elements of the toothbrush. In this embodiment, an oral care toothbrush 10 includes a head 12 and a handle 14. The head 12 may be a refill head and thus be removably connected to the handle 14, or the head may be permanently connected to the handle 14.

The majority of the handle 14 and a portion of the head 12 may be molded from a variety of rigid materials, including plastics, resins, etc., such as, for example, polypropylene. An end portion of the handle 14 opposite the head 12 is attached to an accessory, preferably a toothpick 16 formed of a resilient and soft thermoplastic elastomer. The toothpick 16 may be a refill or replaceable toothpick and thus it may be removably connected to the handle 14. Of course, the toothpick 16 may alternatively be permanently connected to the handle 14. The toothpick 16 provides a mechanism for spot cleaning between teeth. Forming the toothpick 16 of a soft elastomer provides more comfortable interproximal cleaning between teeth. The toothpick 16 could, however, be made of a stiff rigid material similar to the main portion of the handle 14, or could simply be a rubber or elastomeric pick adhered or otherwise mounted to the end of the handle 14.

Portions 18 of the handle 14 may also be formed of a resilient and soft thermoplastic elastomer. The thermoplastic elastomer which forms the toothpick 16 and handle portions 18 may be a thermoplastic vulcanate (TPV) consisting of a mixture of polypropylene and EPDM (ethylene propylene diene monomers) which is available as SANTOPRENE™, described in U.S. Pat. No. 5,393,796, or VYRAM™, another TPV consisting of a mixture of polypropylene and natural rubber. Both SANTOPRENE™ and VYRAM™ are elastomers marketed by Advanced Elastomer Systems. Other suitable elastomers include KRATON™, a brand of styrene block copolymer (SBC) marketed by Shell, and DYNAFLEX G 2706™, a thermoplastic elastomer marketed by GLS Corporation and which is made with KRATON™ polymer.

The handle 14 may further include dimples, bumps, or ridges protruding from portions of its surface, thereby providing a decorative appearance to the handle 14 and enhanced gripping of the handle 14 during use of the toothbrush 10. The dimples may be formed from the same material as the soft elastomer portions 18 of the handle 14 or from the same material as the majority of the handle 14 (e.g., a rigid material such as polypropylene). All or part of the handle 14 could be made of any suitable material, such as plastic, wood, metal or various natural materials which are biodegradable. Preferably, the handle 14 is made of a generally flat or oval shape rather than cylindrical in its gripping portion which would be between the spaced elastomer portions 18, 18 to facilitate the gripping of the handle 14.

Figure 4:
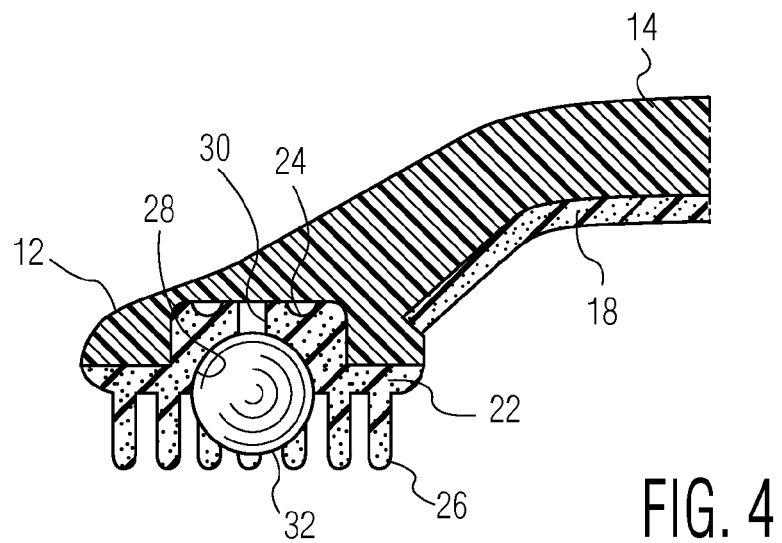
FIG. 4 is a cross-sectional view of the head of the oral care toothbrush of FIG. 1.

As shown in FIG. 4, another portion of the head 12, defining a bristle or cleaning element block 22 of the head 12, may also be formed of a resilient and soft thermoplastic elastomer, such as the thermoplastic elastomer used to form the handle portions 18. The cleaning element block 22 may include one or more depressions 24 provided in a surface 30 thereof with an opening 30 therein that provides a cushioning effect to a rupturable dispenser, preferably a gel capsule 32, contained therein, as described more fully below. The cleaning element block 22 further includes a multitude of cleaning elements 26 which could be conventional filament, preferably nylon, or elastomeric bristles or fingers extending integrally outwardly from the outer surface of the head 12. In the illustrated embodiment as best shown in FIG. 4, all of the cleaning elements 26 extend outwardly from the outer surface of the cleaning element block 22 the same distance so as to create a generally flat surface. Alternatively, however, some of the cleaning elements 26 may be shorter or longer than others of the cleaning elements 26. The variable length of the cleaning elements 26 is illustrated by the dotted out tips 26a in FIG. 8, with only body portions 26b of the cleaning elements 26 shown in solid lines for purposes of clarity and to focus on the variable nature of such elements.

The term "cleaning elements" as used herein is intended to be used in a generic sense as cleaning elements or massage elements arranged in a circular cross-section shape or any type of desired shape, including straight portions or sinusoidal portions. It is to be understood that the specific illustration of the cleaning elements is merely for exemplary purposes. The invention can, however, be practiced with various combinations of the same or different configurations (such as stapled, in-mold tufting (IMT) bristle technology as disclosed in U.S. Pat. Nos. 5,609,890, 5,390,984, and 5,533,791) and/or with the same or different bristle materials (such as nylon bristles, spiral bristles, rubber bristles, etc.). Similarly, while FIGS. 1-4 illustrate the cleaning elements 26 to be generally perpendicular to the outer surface of the head 12, some or all of the cleaning elements 26 may be angled at various angles with respect to the outer surface of the head 12. It is thereby possible to select the combination of configurations, materials and orientations to achieve specific intended results, such as enhanced cleaning, tooth polishing, tooth whitening, massaging of the gums and/or combinations thereof.

It is intended that the cleaning elements 26 be used with the gel capsule 32, which contains the dentifrice described above. In other words, the dentifrice comprising an amount of an abrasive material as described above in a carrier and possibly combined with any of one or more of a flavorant, colorant, sweetener, processing aid and water can be encapsulated within the gel capsule 32. Alternatively, when the dentifrice composition is a solid dentifrice or a gum dentifrice, it can be disposed within or between the cleaning elements 26 in a manner that will be apparent from the description set forth herein. In this manner, the cleaning elements 26 may act as a polisher that will assist and/or activate the dentifrice once the dentifrice is applied to the teeth. The polishing and/or whitening effect of the dentifrice may be further enhanced by creating the cleaning elements 26 out of an elastomeric material, such a thermoplastic elastomer. Elastomeric cleaning elements 26 will act as wipers when rubbed against the surfaces of the teeth.

In other embodiments, the cleaning elements 26 are in the form of a single mass having an irregular outer surface. The single mass may be similar to that of "steel wool" as used in household cleaning or could be part of Velcro® formations, such as hooks and loops. In other embodiments, the cleaning elements 26 may be a single mass of foam for cotton which could be used as a swab for the dentifrice composition having improved stain removal and teeth cleaning efficacy. In such embodiments, the cleaning elements 26 can either be impregnated with the dentifrice composition or could be dipped into the dentifrice composition so as to absorb the material.

As stated above, the cleaning block 22 may include one or more depressions 24 which are designed to receive and retain an oral care dispenser, such as the rupturable gel capsule 32 therein. The rupturable gel capsule 32 encapsulates the dentifrice composition described above.

The one or more depressions 24 can be varied in size so as to accommodate not only varying sized gel capsules 32, but varying quantities of the dentifrice composition, for delivery to the denture as the cleaning elements 26 extending from the cleaning block 22 are applied thereto. While the present invention can be manufactured containing a dentifrice composition as described herein and used repeatedly by the user refilling the dispenser with the dentifrice composition, it is preferably used with one or more gel capsules 32 contained therein. Most preferably, the composition is used with a single gel capsule 32, supplied therewith, so as to be most easily transported, used, and subsequently disposed of. However, it may also be used repeatedly with replaceable gel capsules 32, and then disposed of.

It is preferred that the depression is in the form of a cushioned socket 28 sized and shaped to receive and retain the gel capsule 32, without premature rupture of the gel capsule 32 prior to use thereof during application of the bristle block 22 to the denture and brushing thereof. Cushioning socket 28 opening 30, and the material making up the bristle block 22 provide a cushioning effect for the gel capsule 32 to prevent the gel capsule 32 from rupturing prior to use.

The gel capsule 32 holds and applies the subject dentifrice composition onto the cleaning elements 26 of the toothbrush head 12. Preferably, the gel capsule 32 is a gel capsule having frangible, thin walls that easily rupture or burst when rubbed against the teeth, or dissolve when mixed with the saliva of a user. The materials making up the gel capsule 32 are consumable by the user of the toothbrush 10, eliminating the need for water, a sink, or a waste receptacle to expectorate the gel capsule 32. The dentifrice composition remains in the gel capsule 32 until the toothbrush 10 is ready for use. Preferably, the gel capsule 32 is fully sealed, helping the dentifrice composition remain fresh until use.

In use, the gel capsule 32 would be pressed against the teeth and burst or rupture or dissolve, applying the dentifrice composition over the cleaning elements 26. The user then may brush their teeth with the toothbrush 10. The user may also use the toothpick 16 to clean between teeth, either before or after brushing. After the user has used the toothbrush 10, one may easily and economically dispose of the toothbrush 10, although this is not required since the toothbrush 10 may be reusable as described above.

In one preferred aspect, the entire structure of the toothbrush 10, including the head 12, the handle 14, and the toothpick 16, is molded as one integral structure, using a conventional two-component injection molding operation typically used in the manufacture of toothbrushes. This enables the toothbrush 10 to be economically and quickly manufactured. Although the toothbrush 10 may have a variety of sizes and dimensions, it is preferred that the toothbrush 10 have a small profile, with the head 12 being small enough to cover one tooth at a time and the handle 14 being thinner than conventional, everyday toothbrush handles. The toothbrush 10 is thus readily portable or space saving.

The toothbrush 10 provides many benefits, including the cosmetic benefits of brushing one's teeth in a form that can be used when one is away from home, and away from a water supply. The cosmetic benefits achieved by the toothbrush 10 include the cleaning of debris between teeth with the toothpick 16, broad tooth surface cleaning and/or whitening with the cleaning elements 26 and the dentifrice composition, and breath freshening when the dentifrice composition comprises a flavorant or sweetener as described above.

The cosmetic benefits may further include improved stain removal and teeth cleaning efficacy in an on-the-go type of situation. For example, the toothbrush 10 with a gel capsule 32 containing the dentifrice composition may be used after drinking coffee or tea in order to reduce staining of the teeth that is known to result from those beverages. Furthermore, because the toothbrush 10 is particularly suited for cleaning the front surfaces of the front teeth, which are the portions of the teeth most susceptible to coffee and tea stains, the stain removal efficacy is further improved.

In addition to the cosmetic benefits, the toothbrush 10 also provides economic benefits in the form of an inexpensive toothbrush that is both quickly and economically manufactured. The toothbrush 10 also provides a mechanism for maintaining oral health, without the need for toothpaste, water, mouth wash, and containers to hold the same. Thus, the toothbrush 10 is also very convenient to use.

Although FIGS. 1-4 illustrate a manually-operated, disposable toothbrush, the present invention may also be practiced where the head includes one or more power or electrically operated movable sections carrying cleaning elements. Such movable section may oscillate in a rotational manner or may oscillate linearly in a longitudinal direction with respect to the longitudinal axis of the head or may oscillate linearly in a lateral or transverse direction with respect to the longitudinal axis of the head. The movable section may oscillate in and out in a direction toward and away from the outer surface of the head. The movable section may rock back and forth with respect to the outer surface of the head. The movable section may rotate continuously in the same direction, rather than oscillate. Any suitable drive mechanism may be used for imparting the desired motion to the movable section. Where plural movable sections are used, all of the movable sections may have the same type and direction of movement, or combinations of different movements may be used. Alternatively, the toothbrush may simply comprise a vibratory element, such as a piezoelectric crystal, to cause the head 12 to vibrate during use.

In accordance with one aspect, the cleaning elements may be in the form of bristles made from conventional materials, such as nylon, as well as from a combination of materials so as to provide the proper stiffness in an economical manner. Preferably, the cleaning elements are made of a flexible resilient material, such as TPE and a lesser expensive material such as LLDPE (linear low density polyethylene) or EVA (ethylene vinyl acetate) or a TPE. The cleaning elements could be made of a blend of TPE and either LLDPE, EVA, or polypropylene. Preferably, the two materials are combined to provide a stiffness of less than 600 MPa. The blend of materials would give the properties of conventional nylon bristles, while offering reduced costs. For example, there would be lower manufacturing costs by injection molding instead of conventional bristle tufting. Alternatively the resilient material could be a single material, such as hard TPE (i.e. Shore A 80 hardness), straight LLDPE or straight EVA.

The cleaning elements may be of any desired shape. For example, the cleaning elements could be of cylindrical shape having a uniform diameter throughout their length. Alternatively, the cleaning elements could taper from the root of each cleaning element where it extends from the head 22 to its outer cleaning end. Since a preferred practice is to provide a small lightweight toothbrush, the dimensions of the various components of the toothbrush 10 are preferably small. Thus, for example, each of the cleaning elements 26 may extend outwardly from the outer surface of the cleaning block 12 a distance no greater than 10 mm and preferably no greater than 8 mm and most preferably no greater than 6 mm. Where tapered cleaning elements are used the root diameter should be no greater than 1.5 mm, preferably no greater than 1 mm, most preferably no greater than 0.7 mm or no greater than 0.5 mm or no greater than 0.3 mm. The diameter could then decrease in size to no greater than 0.2 mm at a distance of no greater than 6 mm from the base of the cleaning element. The taper relationship of diameter at a distance location above the root diameter could be a range of no greater than 1 mm at a distance of no greater than 10 mm, preferably no greater than 0.6 mm at a distance of no greater than 8 mm, most preferably no greater than 0.2 mm at a distance of no greater than 6 mm. Preferably, the length of the entire toothbrush 10 is no greater than 12.7 cm (5 inches), preferably no greater than 10.2 cm (4 inches), and more preferably no greater than 9.5, 7.6, or 6.4 cm (3.75 or 3 or 2.5 inches), and may be in the range of 5.1 to 10.1 cm (2 to 4 inches).

Figure 8:
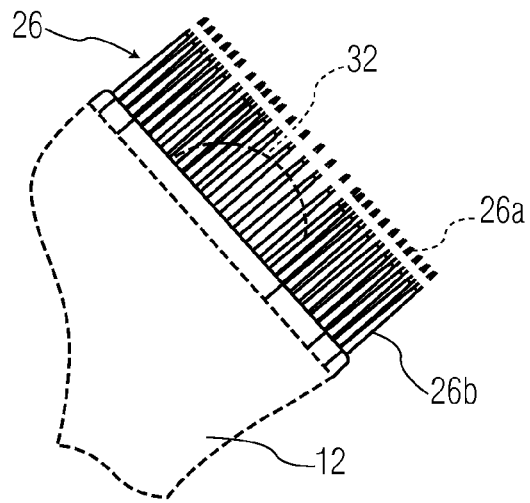
FIG. 8 is a side view of a head of an oral care toothbrush according to an embodiment with only portions of the cleaning elements shown in solid lines for purposes of focus and clarity.

As illustrated in FIGS. 1 and 4 the cleaning elements 26 define a cleaning field in the head and the dispenser 32 is mounted within this cleaning field. The cleaning elements 26 preferably extend outwardly from the cleaning block 22 to be approximately flush with the outer surface of the gel bead or capsule 32, as shown in FIG. 4. The invention, however, can also be practiced where the cleaning elements extend either a greater distance or a lesser distance than the dispenser 32 as shown in FIG. 8. Since toothbrush 10 is intended to be both small and lightweight, it is preferred that toothbrush 10 weigh no more than 3 grams. The small size is such that it can be held completely within the palm of an adult user. The head 12 is of a size that it would correspond to the size of an individual tooth or an individual tooth and the interproximal areas. The head 12 could be made of any suitable shape and is preferably of circular or oval shape having a maximum lateral dimension or diameter of no greater than 13 mm, preferably no greater than 12 mm, and most preferably no greater than 11 mm. Where the head 12 is of non-circular shape its maximum lateral dimension is 14 mm.

Figure 2:
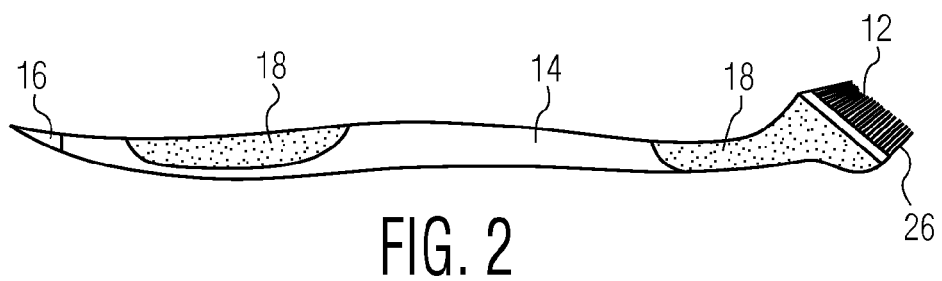
FIG. 2 is a side view of the toothbrush of FIG. 1.
Figure 3:
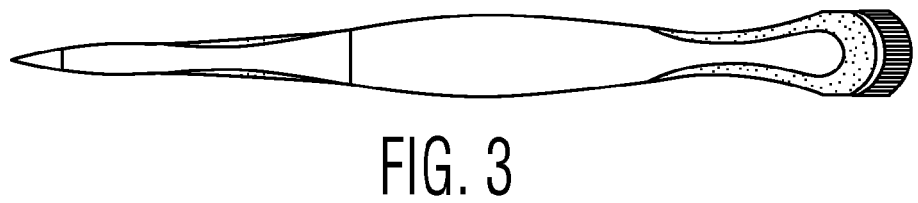
FIG. 3 is a rear view of the toothbrush of FIG. 1.

As shown in FIG. 2, the head 12 is preferably at an angle between 0° and 90° to the longitudinal axis of the handle 14. The preferred angle is from 20° to 70° and more preferably from 30° to 60°. The cleaning elements 26 could be perpendicular to the outer surface of the head 12 or could also be at an angle to the outer surface such as in the range of 60° to 90° or in the range of 75° to 90°.

In one aspect, the cleaning elements 26 could be hollow, such as hollow bristles, which are capable of absorbing the dentifrice composition discussed above by capillary action. In one aspect where the cleaning elements 26 are used to dispense the dentifrice composition, the cleaning elements 26 themselves may be considered oral care dispensers without requiring additional dispensers such as capsule 32. In this aspect, preferably the dentifrice composition described above will be positioned within the cleaning elements 26 prior to use of the toothbrush 10. Where specific parameters and characteristics have been given for cleaning elements, the invention could be practiced where other cleaning elements do not include those parameters and characteristics.

Figure 5:
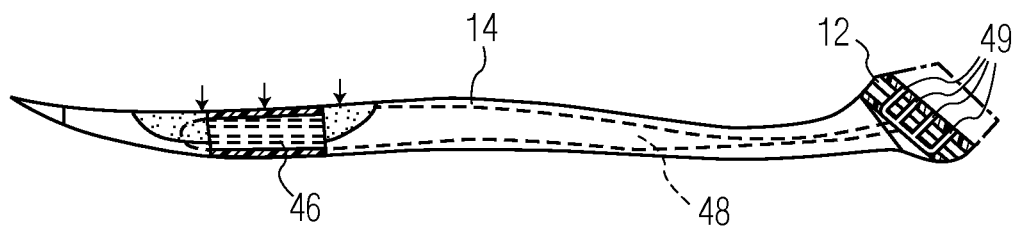
FIG. 5 is a side view partly in section of an oral care toothbrush comprising a reservoir comprising a dentifrice composition in accordance with another embodiment.

FIG. 5 illustrates another aspect wherein the handle 14 has a hollow chamber 46 in which the dentifrice composition described above could be contained. The chamber 46 leads to a passageway 48 which extends to the head 12 and terminates in a plurality of branches 49 at the outer surface of the head 12 within the cleaning field. In order to dispense the oral care material located in the chamber or reservoir 46, the handle 14 would have sufficient resiliency so that it can be squeezed thereby forcing the dentifrice composition from the handle 14 to the head 12 into a dispensing cavity or one or more dispensing openings.

Figure 9:
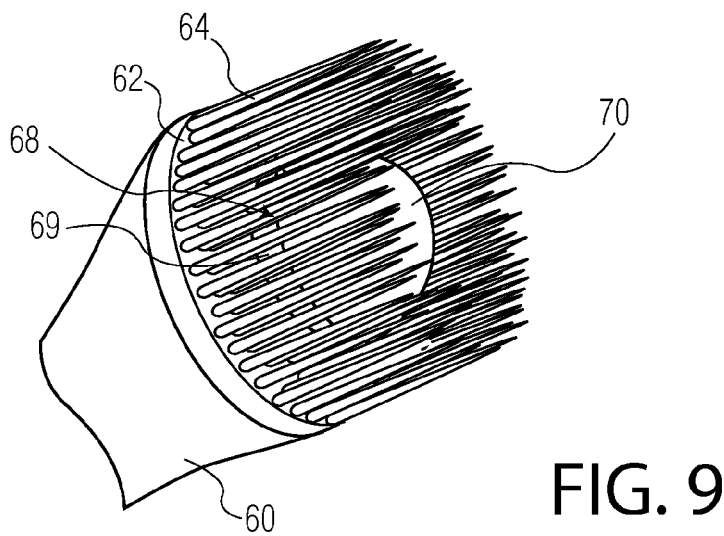
FIG. 9 is a perspective view of a head of an oral care toothbrush comprising a capsule comprising a dentifrice composition in accordance with a further embodiment.
Figure 10:
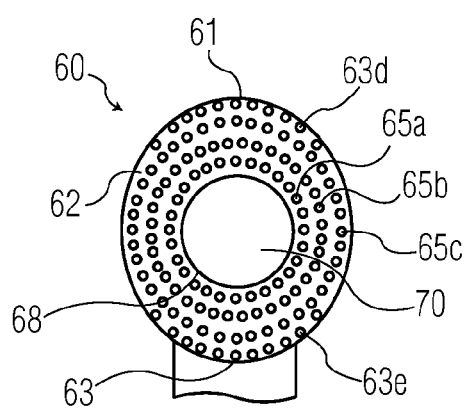
FIG. 10 is a planar front view of the head of FIG. 9.

FIGS. 9 and 10 illustrate a head 60 according to another embodiment in which the head 60 has an outer surface 62, a plurality of cleaning elements 64 extending from a portion of the outer surface 62, and a raised socket 68 extending from another portion of the outer surface 62. The socket 68 is preferably formed from the same material as the outer surface 62, and is preferably integrally formed with the outer surface 62 such as by molding or the like. The socket 68 extends outwardly relative to the outer surface 62 by an upstanding wall 69, and includes a seat to accommodate an oral care dispenser such as a bead or capsule 70 as discussed herein. The capsule 70 preferably encapsulates the dentifrice composition described. The raised socket 68 positions the capsule 70 closer to the edges of the cleaning elements 64 to facilitate contact between the capsule 70 and the user's teeth and to encourage rupturing of the capsule 70 early in the brushing process. The socket may also position the capsule 70 beyond the cleaning elements 64 as discussed above, which would encourage even greater and immediate contact with the user's teeth.

The cleaning elements 64 may comprise a variety of configurations as discussed above, such as a circular configuration as shown in FIG. 1. FIG. 10 illustrates an example of an oval configuration, wherein the cleaning elements 64 are arranged in a plurality of concentric rings 65a, 65b, 65c, surrounding the socket 68. One of such rings is a partial ring comprised of partial ring sections 65d, 65e defined along the upper and lower edges 61, 63 of the outer surface 62 of the head 60, which sections 65d, 65e comprise the equivalent of a so-called power tip that is designed to provide a cleaning edge that extends beyond the majority of the field of cleaning elements for increased efficacy.

Any suitable methods may be used for forming the toothbrush 10 and its various components. For example, multi-component injection molding could be used to integrally couple various components such as the cleaning elements 26 and the head 12 and/or the handle 14. This could be done in an automated or multiple step process. The handle 14 could be rotocast blow molded to form a hollow squeeze handle that would be usable in the embodiment shown in FIG. 5.

Figure 6:
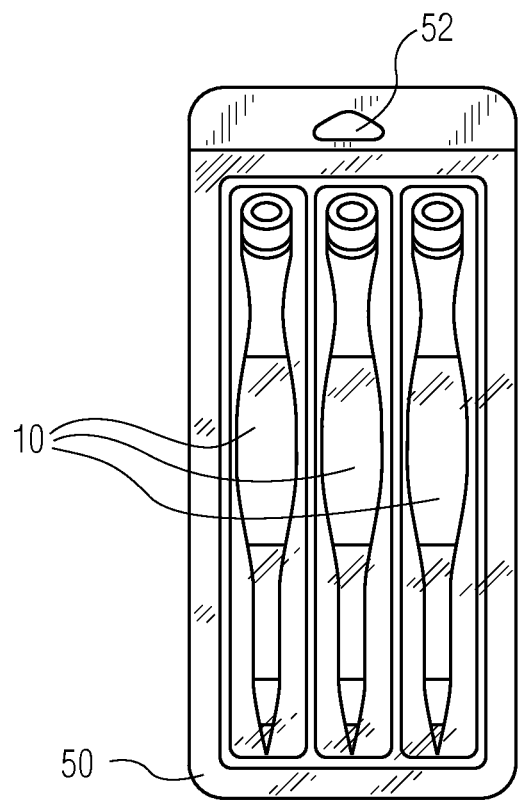
FIG. 6 is a front view showing multiple toothbrushes in accordance with an embodiment in a packaged or display condition.
Figure 7:
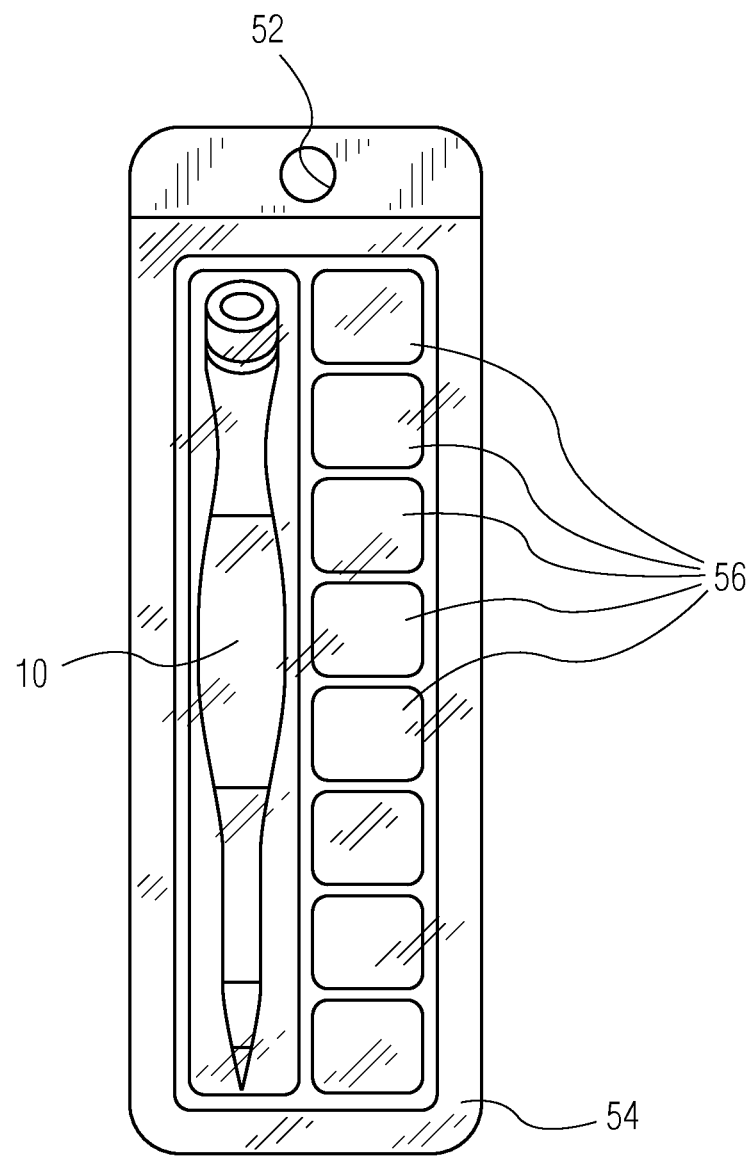
FIG. 7 is a front view showing a single toothbrush in accordance with an embodiment in a packaged or display condition along with accessories.

FIGS. 6-7 show different manners of packaging toothbrushes. As shown in FIG. 6, for example, a single package 50 could contain a plurality of toothbrushes 10 all of which could be the same or could differ from each other. The package 50 could be of any conventional construction, such as a blister pack, which might include a hole 52 to permit the package to be hung for display purposes.

FIG. 7 illustrates a variation wherein the package 54 includes one or more toothbrushes 10 and a plurality of other components 56 which could be accessories or dispensers or other components. The components could include a replaceable capsule containing the dentifrice composition described above. Preferably, the package 50 or 54 would be hermetically sealed to assure freshness. Such hermetic sealing is particularly desired to prevent moisture from reaching the gel capsule 32 and causing the capsule 32 to burst.

Figure 11:
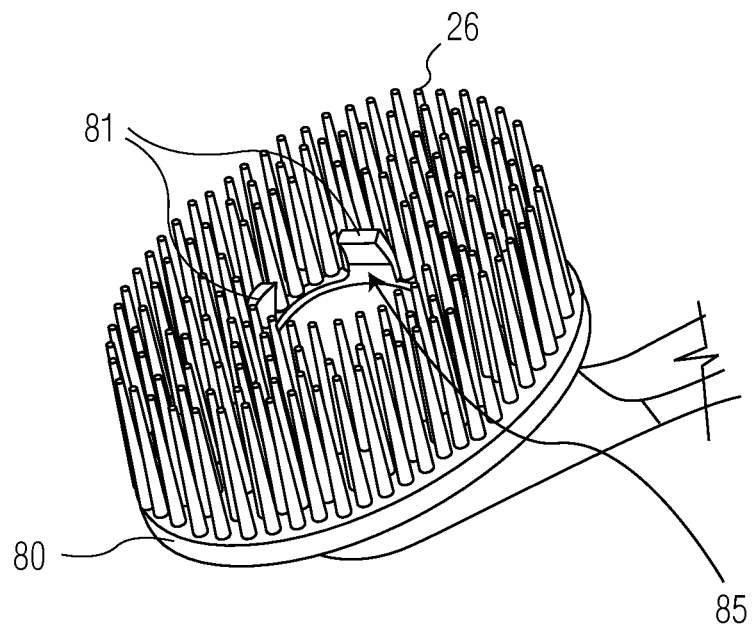
FIG. 11 is a perspective view of a toothbrush head that is adapted to retain a capsule comprising a dentifrice composition in accordance with yet another embodiment.

FIG. 11 illustrates another variation in which the head or carrier 80 may have an oval shape, and which may have a series of retaining members 81, such as prongs or biasing members, to hold an oral care dispenser, such as a bead of packed dentifrice of the dentifrice composition described above or a capsule (not shown in the figure), in place prior to use. The retaining members 81 may help retain the bead or capsule at a higher elevation with respect to the field of oral care elements (e.g., bristles 26), to expose more surface area of the bead, dispenser or capsule 32 to the user's saliva to improve the "mouth-feel" and expedite the dissolving of the bead, dispenser or capsule. As illustrated, the retaining members 81 may retain the bead, dispenser or capsule beneath the distal ends of the bristles 26, so as to keep the bead, dispenser or capsule submerged within the field of bristles 26, such that the bristles extend beyond the bead, dispenser or capsule at the bristles' distal ends.

The retaining members 81 may be made of the same material as the bristles 26, or alternatively they may be made of a different material having greater rigidity than the bristles 26. In one construction, the retaining members 81 may be made of the same material as elastomer portions 18 of the handle 14 as described above in FIGS. 1-4.

Figure 12:
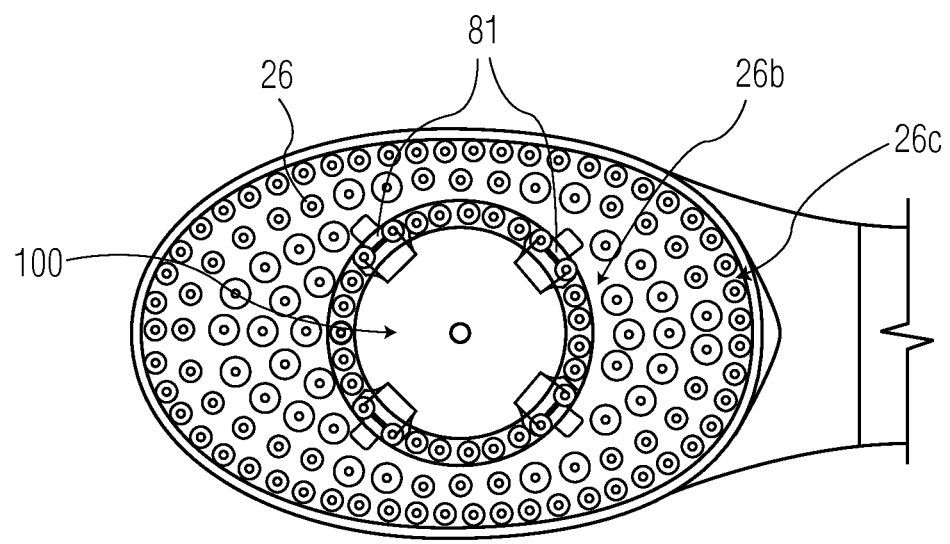
FIG. 12 is a planar front view of the head of FIG. 11.

The number of retaining members 81 used may vary depending on the type of bead or capsule, and the amount of retention force assistance. As illustrated in FIG. 12, four retaining members 81 may be used at four cardinal points around the perimeter of the bead or capsule. Of course, greater or fewer retaining members 81 may be used. For example, some embodiments might use three retaining members 81 at triangular points around the perimeter, while other embodiments might use five, six, or more prongs around the perimeter. The retaining members 81 may be positioned such that the bead or capsule is held in a centered position with respect to the bristles 26.

As also shown in FIG. 12, the bristles 26 may vary in diameter at their proximate ends, so that bristles in different areas of the field have different thicknesses and rigidity or axial stiffness as measured from the longitudinal axis of the bristle. In such a construction, inner or central region bristles 26b are stiffer than the outer or peripheral region bristles 26c. The bristles 26 of the carrier 80 may taper towards their distal ends, as seen in FIG. 11.

With reference to FIG. 12, the variable stiffness arrangement of the field of bristles 26 forms a structure for incremental radial flow control of the dentifrice composition during a brushing operation for efficient cleaning. The bristles surrounding retaining members 81 are independently flexible. In this regard, during a brushing operation, the free ends (e.g., tip) of the stiffer bristles 26b bend relative to their respective vertical axis less than the outer bristles 26c (e.g., bristles near the periphery). Hence, a portion of the dentifrice stays longer in the central region of the brush head by reduced dynamic bending or action of the stiffer bristles.

The sweeping or oscillating motion of the carrier 80 transfers a portion of the retained the dentifrice composition to the outer region of the carrier 80. While the outer bristles 26c are less stiff, the dynamic bending relative to their vertical axis additionally causes the outer bristles to receive a portion of the dentifrice composition from the central region of the carrier 80. In this way, the bristle field provides a limited and controlled flow of the dentifrice or other oral care material to the outer bristles and maintains sufficient flexibility to provide greater user comfort and improved cleaning of the oral tissues.

Figure 13:
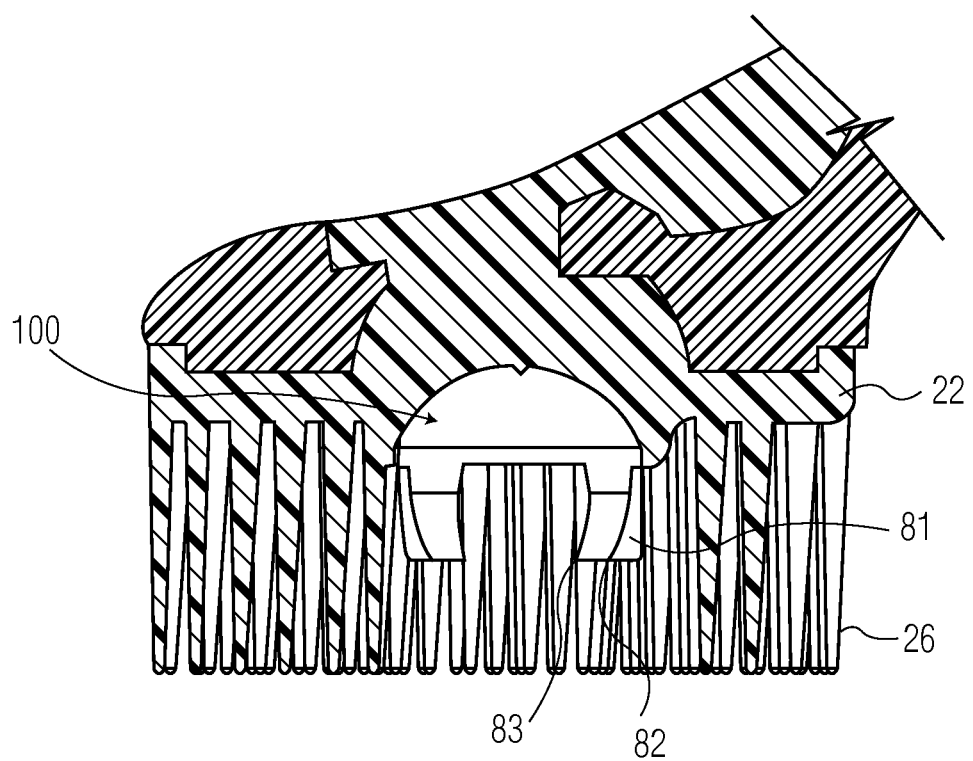
FIG. 13 is a cross-sectional side view of the head of FIG. 11.
Figure 14:
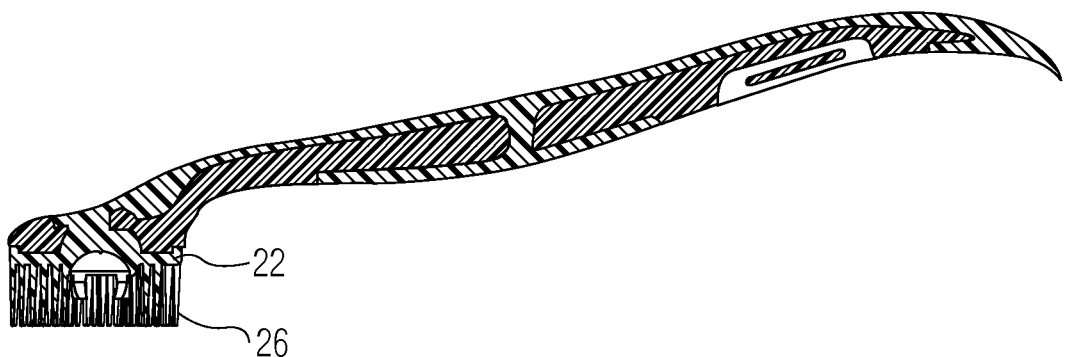
FIG. 14 is a cross-sectional side view of a toothbrush having a head that is adapted to retain a capsule comprising a dentifrice composition in accordance with still another embodiment.

With reference to FIGS. 11-14, in one construction, a basin, or cavity 100 is provided in the carrier 80 below the dispenser 32. As can as seen in FIGS. 13 and 14, the basin 100 can be a concaved structure or hemispherical structure disposed in the interior area, beneath and between the retaining members 81. While a concaved structure is shown, other shapes for the basin 100 are possible, such as a triangular prism, a square prism or a rectangular prism. The basin 100 serves to retain a portion of the dentifrice composition from the dispenser 32 to extend the beneficial cleaning effects of the dentifrice composition during brushing. In this regard, the sweeping or oscillating motion of the carrier 80 transfers a portion of the retained dentifrice composition to inner region bristles 26b of the carrier 80.

In one construction, the retaining members 81 are columnar-like structures that extend upwardly from the carrier 80. The retaining members 81 may curve inwardly to further assist in holding the bead or capsule in place. FIG. 13 illustrates a close-up cross-sectional view, showing such curved retaining members 81. Such curved retaining members 81 may have a length that extends more than halfway up (or down, depending on angle of view) the diameter of the bead or capsule 32 for retention. Hence, a length portion of the retaining members may be acutely disposed with respect to a vertical axis of the carrier 80 for retention. The combination of retaining members 81 provides a compressive force to hold the dispenser 32 in place. The inwardly disposed engaging surface 85 is generally smooth to reliably resist prematurely rupturing the dispenser 32 before use. (See FIG. 11). Also, the smooth and curved characteristic of the engaging surface 85 provides for a generally uniform distribution of pressure on the surface of the dispenser 32. This construction thus reduces thin wall stress on the surface of the dispenser 32 to reliably resist prematurely rupturing the dispenser 32 before use. For example, shock forces acting on the toothbrush can be dissipated during transport operations.

The retaining members 81 may assist in rupturing the bead or capsule during brushing, and may have a flat surface at a distal end 82 to form a corner edge 83 against the bead or capsule for this purpose. With reference to FIGS. 12 and 13, some of the bristles 26 may extend from the retaining members 81. In this construction, a portion of the base of the bristle extends from a rear/back of the retaining member 81. This provides a compact space-saving head structure and also provides flow control benefits of the dentifrice composition in the bristle field.

As illustrated in FIG. 13, the block 22 may be made of the same material as some or all of the bristles 26, as discussed above, which may be a different material from other portions of the handle 14. Alternatively, the handle 14 and block 22 may be made of the same material, with the bristles 26 being made of a different material.

FIG. 14 illustrates a cross-sectional view of a toothbrush having the head or carrier structure shown in FIGS. 11-13. The carrier 80 may be angled at a 10° angle with respect to the handle, representing a less-angled head than that shown in previous figures. An angle ranging from 8° to 12° may assist in improving a user's brushing technique. As with FIG. 13, FIG. 14 also shows an example arrangement of materials, where the block 22 may be made of the same materials as some or all of the bristles 26 and portions of the handle. Alternatively, the handle may be made of the same material as the block 22 and/or bristles 26.

Hence, in some embodiments, an oral care implement may include a rupturable dispenser with the dentifrice composition, as a connected unit or the various other combinations of components and materials as described. A toothbrush may have a toothpick which enables cleaning between the teeth. A dispenser containing a dentifrice, such as the dentifrice composition described herein, or other oral care material can be connected in the bristle or cleaning element portion of the toothbrush for dispensing the dentifrice composition to the teeth. In one construction, the oral care elements are configured to slow a radial flow of the dentifrice composition released from the dispenser near an interior region of the carrier and increase a radial flow of the oral care material away from the interior region.

The invention has been described above with respect to various preferred aspects; however it is to be understood the invention is not limited to the disclosed embodiments. Variations and modifications that will occur to the person of skill in the art are also part of the invention, which is defined in the appended claims.

What is claimed is:

1. A toothbrush comprising:
 a handle;
 a head mounted to the handle, the head comprising an outer surface and a plurality of tooth cleaning elements extending outwardly from the outer surface; and
 a dentifrice composition positioned on the head, wherein the dentifrice composition comprises an orally acceptable carrier and 1 to 10 wt % abrasive, such that the total amount of abrasive delivered per application is 2 mg to 8 mg, the abrasive having a weight mean particle size in the range of 3 to 7 μm, with at least 90% of the particles by weight having a size below 16 μm, and wherein the composition does not contain antibacterial agents, malodor prevention agents, anti-caries agents, whitening agents, tartar control agents, foaming agents, anti-calculus agents, fluorides, anti-microbial agents, or anti-inflammatory agents,
 wherein the orally acceptable carrier comprises a triglyceride.

2. The toothbrush of claim 1, wherein the total amount of abrasive delivered per application is 3 to 6 mg.

3. The toothbrush of claim 1, wherein the dentifrice composition further comprises 5% to 25% by weight of a flavoring material and 0.1% to 5% by weight of a sweetening agent.

4. The toothbrush of claim 1, wherein the dentifrice composition comprises about 75 weight % triglyceride, about 15 weight % flavor, about 5 weight % of the abrasive, about 0.5 weight % sweetener, and about 4.5 weight % ethanol.

5. The toothbrush of claim 1, wherein the dentifrice is encapsulated.

6. The toothbrush of claim 5, wherein the dentifrice is encapsulated in gelatin.

7. The toothbrush of claim 1 further comprising a dispenser positioned within the cleaning elements, the dispenser containing the dentifrice composition.

8. The toothbrush of claim 7, wherein the dispenser is a capsule and the dentifrice composition is encapsulated within the capsule in liquid form.

9. The toothbrush of claim 1, wherein the cleaning elements are constructed of an elastomeric material.

10. The toothbrush of claim 1, wherein the dentifrice composition is encapsulated within a gelatin capsule, the gelatin capsule positioned within and surrounded by the cleaning elements, wherein the cleaning elements are elastomeric.

11. The toothbrush of claim 1, wherein the cleaning elements comprise the dentifrice composition.

12. An encapsulated dentifrice composition suitable for use with the toothbrush of claim 1, comprising an orally acceptable carrier and 1 to 10 wt % abrasive, the dentifrice comprising 2 mg to 8 mg of abrasive, the abrasive having a weight mean particle size in the range of 3 to 7 μm, with at least 90% of the particles by weight having a size below 16 μm, wherein the composition does not contain antibacterial agents, malodor prevention agents, anti-caries agents, whitening agents, tartar control agents, foaming agents, anti-calculus agents, fluorides, anti-microbial agents or anti-inflammatory agents, and wherein the orally acceptable carrier comprises a triglyceride.

13. The dentifrice of claim 12, comprising 3 to 6 mg of abrasive.

14. The dentifrice of claim 12, wherein the dentifrice composition further comprises 5% to 25% by weight of a flavoring material and 0.1% to 5% by weight of a sweetening agent.

15. The dentifrice of claim 12, wherein the dentifrice composition comprises about 75 weight % triglyceride, about 15 weight % flavor, about 5 weight % of the abrasive, about 0.5 weight % sweetener, and about 4.5 weight % ethanol.

16. The dentifrice of claim 12, wherein the dentifrice is encapsulated in gelatin.

17. A method of making a dentifrice composition comprising mixing an orally acceptable carrier, flavors, sweeteners, and optionally, a processing aid to form a liquid mixture, and adding to the liquid mixture 1 to 10 wt % abrasive having a mean particle size in the range of 3 to 7 µm, with at least 90% of the particles by weight having a size below 16 µm, without mixing or adding antibacterial agents, malodor prevention agents, anti-caries agents, whitening agents, tartar control agents, foaming agents, anti-calculus agents, fluorides, anti-microbial agents or anti-inflammatory agents, the method further comprising encapsulating the dentifrice composition in a gelatin capsule, wherein the dentifrice comprises 2 mg to 8 mg of the abrasive, and wherein the orally acceptable carrier comprises a triglyceride.

18. An encapsulated dentifrice composition, prepared in accordance with the method of claim 17.

19. A method of removing stain from teeth comprising applying a dentifrice composition to the teeth in a manner that delivers 2 mg to 8 mg of an abrasive to the teeth, wherein the dentifrice composition comprises an orally acceptable carrier and 1 to 10 wt % abrasive, the abrasive having a weight mean particle size in the range of 3 to 7 µm, with at least 90% of the particles by weight having a size below 16 µm, wherein the composition does not contain antibacterial agents, malodor prevention agents, anti-caries agents, whitening agents, tartar control agents, foaming agents, anti-calculus agents, fluorides, anti-microbial agents or anti-inflammatory agents, and wherein the orally acceptable carrier comprises a triglyceride.

20. The method of claim 19, wherein the total amount of abrasive delivered per application is 3 to 6 mg.

21. The method of claim 19, wherein the dentifrice further comprises 5% to 25% by weight of a flavoring material and 0.1% to 5% by weight of a sweetening agent.

22. The method of claim 19, wherein the dentifrice composition comprises about 75 weight % triglyceride, about 15 weight % flavor, about 5 weight % of the abrasive, about 0.5 weight % sweetener, and about 4.5 weight % ethanol.

23. The method of claim 19, wherein the dentifrice is encapsulated.

24. The method of claim 23, wherein the dentifrice is encapsulated in gelatin.

* * * * *